United States Patent [19]

Blechschmitt et al.

[11] 4,077,984

[45] Mar. 7, 1978

[54] MANUFACTURE OF PHTHALIC ANHYDRIDE FROM o-XYLENE OR NAPHTHALENE

[75] Inventors: Kurt Blechschmitt, Schifferstadt; Peter Reuter, Bad Durkheim; Friedrich Wirth; Paul Hornberger, both of Ludwigshafen, all of Germany

[73] Assignee: BASF Aktiengesellschaft, Ludwigshafen (Rhine), Germany

[21] Appl. No.: 731,005

[22] Filed: Oct. 8, 1976

[30] Foreign Application Priority Data

Oct. 16, 1975 Germany .............. 2546268

[51] Int. Cl.$^2$ .......................... C07D 307/89
[52] U.S. Cl. .................. 260/346.4; 252/435
[58] Field of Search ........................ 260/346.4

[56] References Cited

U.S. PATENT DOCUMENTS

| | | | |
|---|---|---|---|
| 2,294,130 | 8/1942 | Porter | 260/346.4 |
| 3,898,249 | 8/1975 | Felice et al. | 260/346.4 |
| 4,007,136 | 2/1977 | Blechschmitt et al. | 260/346.4 |

FOREIGN PATENT DOCUMENTS

2,212,947  9/1973  Germany .............. 260/346.4

*Primary Examiner*—Richard L. Raymond
*Attorney, Agent, or Firm*—Keil, Thompson & Shurtleff

[57] ABSTRACT

A process for the manufacture of phthalic anhydride by oxidizing o-xylene and/or naphthalene over a supported catalyst containing vanadium pentoxide and titanium dioxide, at from 350° to 500° C, in which the o-xylene or naphthalene is passed, with an oxygen-containing carrier gas, over the catalyst, and in which the catalyst in the first 25–50 per cent by volume of the total catalyst volume, in the direction of flow of the mixture of o-xylene or naphthalene and carrier gas, contains from 0.01 to 0.3 per cent by weight, based on titanium dioxide, of rubidium, but no phosphorus, in the active composition, while the remainder of the catalyst contains from 0.02 to 0.8 per cent by weight, based on titanium dioxide, of phosphorus, but no rubidium, in the active composition.

5 Claims, No Drawings

MANUFACTURE OF PHTHALIC ANHYDRIDE FROM O-XYLENE OR NAPHTHALENE

The present invention relates to an advantageous process for the manufacture of phthalic anhydride by oxidizing o-xylene or naphthalene over a supported catalyst containing vanadium pentoxide and titanium dioxide.

It is known that phthalic anhydride is manufactured, in a large-scale industrial process, by catalytic oxidation of o-xylene or naphthalene with air in a fixed bed tubular reactor. Particularly suitable catalysts for this process are supported catalysts which comprise an inert carrier of spherical particles, carrying a thin layer of a catalytic composition of vanadium pentoxide and titanium dioxide. Such catalysts are disclosed, for example, in German Patent No. 1,442,590. Supported catalysts in which the catalytic composition is phosphorus-modified have also been used (German Laid-Open Application No. 1,769,998).

The procedure followed in these conventional processes is generally to pass a mixture of an oxygen-containing carrier gas, e.g. air, and the hydrocarbon to be oxidized through a plurality of tubes located in the reactor and containing the catalyst. The temperature is regulated by surrounding the tubes by a salt melt, in which a temperature of from 350° to 420° C is maintained. With this procedure, undesirable by-products are formed, which are difficult to separate from the desired phthalic anhydride and detract from the quality of the latter. In the case of the manufacture of phthalic anhydride from o-xylene, these by-products are above all aldehydes, e.g. phthalide, whilst when using naphthalene as the starting material the impurities in particular comprise naphthoquinone.

The amount of these by-products formed is the greater, the higher is the content of hydrocarbon, to be oxidized, in the air used. However, high values of these contents are desirable for an economical process of manufacture. By high contents there are meant contents which exceed the lower explosive limit of the mixture of air and the hydrocarbon, e.g. contents of from 44 to 100 g of o-xylene or naphthalene per cubic meter of air.

The formation of the by-products can be repressed by, for example, carrying out the oxidation at higher temperatures, with lower gas throughputs (longer residence times) or with lower hydrocarbon contents of the air. However, this reduces the yield of phthalic anhydride and the reactor throughput.

The use of catalysts in which the catalytic composition has been modified with various additives in order to reduce side-reactions has also been proposed. However, this again does not produce the desired success. Either excessively active catalysts were obtained, which only tolerate a low hydrocarbon content in the air and give poor yields, or the activity of the catalysts was too low, thereby giving good yields but heavy contamination with by-products and hence a phthalic anhydride of poor quality.

It is an object of the present invention to provide a process for the manufacture of phthalic anhydride which permits achieving a high yield and purity of the product even at high hydrocarbon contents of the carrier gas.

We have found that this object is achieved and that particularly advantageous results are obtained in the process of manufacture of phthalic anhydride by oxidizing o-xylene and/or naphthalene over a supported catalyst coated with a catalytic composition containing vanadium pentoxide and titanium dioxide, at from 350° to 500° C, the o-xylene or naphthalene being passed, with an oxygen-containing carrier gas, over the catalyst, if the catalyst of the first 25 – 50 percent by volume of the total catalyst volume, in the direction of flow of the mixture of o-xylene or naphthalene and carrier gas, contains from 0.01 to 0.3 percent by weight, based on titanium dioxide, of rubidium, but no phosphorus, in the active composition, whilst the remainder of the catalyst contains from 0.02 to 0.8 percent by weight, based on titanium dioxide, of phosphorus, but no rubidium, in the active composition.

In the new process, the catalytic oxidation of the hydrocarbons is carried out, for example, by the conventional method in a tubular reactor, with salt bath cooling, at from 340° to 500° C, preferably from 350° to 400° C. The tubes of the reactor, which suitably have a diameter of from 18 to 40 mm and a length of from 2 to 3.5 m, are filled with the catalyst. The catalyst is a supported catalyst which suitably consists of a catalytically inert carrier, with particles suitably of diameter from 3 to 13 mm, carrying a thin layer of the catalytic composition. The carrier is, for example, spherical or, advantageously, ring-shaped, and consists of sintered or fused silicates, porcelain, alumina, silicon carbide or quartz. The catalytic composition, of which a layer suitably of thickness from 0.05 to 1 mm if present on the carrier, contains, for example, from 1 to 30 percent by weight of vanadium pentoxide and from 70 to 99 percent by weight of titanium dioxide. It may in addition contain small amounts, e.g. up to 5 percent by weight, based on the catalytic composition, of antimony, zirconium or tin, for example in the form of their oxides. The catalytic composition suitably accounts for from about 3 to 50 percent by weight of the finished supported catalyst.

According to the invention, the first 25–50, preferably 30–45, percent by volume of the total volume of the catalyst, in the direction of flow of the mixture of the hydrocarbon and oxygen-containing carrier gas, comprise a catalyst which contains from 0.01 to 0.3, preferably from 0.05 to 0.22, percent by weight, based on titanium dioxide, of rubidium in the active composition, but contains no phosphorus. The remainder of the catalyst contains from 0.02 to 0.8, preferably from 0.05 to 0.6, percent by weight, based on titanium dioxide, of phosphorus, in the active composition, but contains no rubidium. Accordingly, the catalyst charge consists of two layers, namely the catalyst layer containing rubidium and the catalyst layer containing phosphorus. However, the catalyst can also be so arranged that the first catalyst layer, which contains rubidium but no phosphorus, consists of two or more (sub-) layers of a catalyst whereof the rubidium content decreases, from layer to layer, in the direction of flow of the reaction gases. Equally, the catalyst layer containing phosphorus can consist of two or more (sub-) layers of a catalyst whereof the phosphorus content increases in the direction of flow. The catalyst layers can be accommodated in one reactor or in, for example, two reactors in series. The only decisive factor is the spatial arrangement of the catalysts relative to the direction of flow of the reaction gases. If the process is carried out in a conventional tubular reactor, the tubes of which are, for example, from 2 to 3.5 m long, and in which the reaction gases flow downward in the conventional manner, the tubes are first filled, for example to a height of from 0.99 to 2.24 m, with the phosphorus-containing catalyst, and the rubidium-containing catalyst is then placed on top, its height being, for example, from 0.60 to 1.44 m. The total height of the catalyst layers in the tubes is suitably from about 1.80 to 3.50 m, preferably from 2.60 to 3.20 m.

The supported catalyst is manufactured, for example, by applying the active composition to the carrier by conventional methods. For example, vanadium pentoxide or a vanadium compound which is converted to vanadium pentoxide on heating, e.g. ammonium vanadate, or vanadium oxalate, formate, acetate, tartrate or salicylate, is mixed with the finely divided titanium dioxide in water or an organic solvent, e.g. formamide, diethylacetamide, ammonium thiocyanate, molten urea or an alkanol, the suitable rubidium compound or phosphorus compound also being admixed, and the mixture, which in most cases has a pasty consistency, is sprayed, for example in a coating drum, onto the carrier which has been preheated at from 100° to 450° C. The finely divided titanium dioxide is obtained, for example, by milling, advantageously in a colloid mill.

Examples of suitable rubidium compounds are rubidium sulfate, rubidium oxide, rubidium carbonate, rubidium acetate and rubidium nitrate. Apart from rubidium sulfate, these compounds are converted to the oxide at elevated temperatures. The rubidium is present in the catalyst as rubidium oxide, rubidium sulfate or rubidium vanadate. Examples of suitable phosphorus compounds are ammonium phosphate, phosphoric acid, phosphorous acid and phosphoric acid esters. Titanium dioxide is preferably employed in the form of anatase, which advantageously has an inner surface area of from 3 to 100 $m^2/g$, preferably from 7 to 50 $m^2/g$, and a particle size of less than 1 $\mu$, e.g. from 0.4 to 0.8 $\mu$.

The new process gives phthalic anhydride in good quality and high yield. The particular and surprising advantage is that the high yield and quality are achieved even at relatively high contents of o-xylene or naphthalene in the air used, e.g. at contents lying within the explosive limits, such as contents of up to 100 g, preferably from 44 to 80 g, of o-xylene or naphthalene per cubic meter (S.T.P.).

EXAMPLE 1

(a) Manufacture of the catalyst I:

600 g of steatite rings having an external diameter of 8 mm, a length of 6 mm and a wall thickness of 1.5 mm, are heated at 260° C in a coating drum and sprayed with a suspension consisting of 400 g of anatase having an inner surface area of 11 $m^2/g$, 73.2 g of vanadyl oxalate (vanadium content corresponding to 41% of $V_2O_5$), 500 g of water, 100 g of formamide and 1.09 g of rubidium carbonate until the weight of catalytic composition applied is 10% of the total weight of the catalyst. The catalytic composition applied in this way consists of 0.202 percent by weight of rubidium oxide (corresponding to 0.186 percent by weight of rubidium), 7.0 percent by weight of vanadium pentoxide and 92.84 percent by weight of titanium dioxide, and contains 1 atom of rubidium per 35.3 atoms of vanadium. Based on anatase, the rubidium content is 0.20 percent by weight.

(b) Manufacture of the catalyst II:

The procedure described under a is followed, but instead of rubidium carbonate 4.87 g of ammonium hydrogen phosphate are added. In the finished catalyst, the weight of the composition applied accounts for 10 percent of the total weight of the catalyst. The catalytic layer consists of 0.3 percent by weight of phosphorus, 7.0 percent by weight of vanadium pentoxide and 92.7 percent by weight of titanium dioxide. The phosphorus content, based on anatase, is 0.32%.

(c) Oxidation 1.60 m of catalyst II, followed by 1.20 m of catalyst I, are introduced into a 3.25 m long iron tube having an internal diameter of 25 cm. The iron tube is surrounded by a salt melt to regulate its temperature. 4.5 cubic meters (S.T.P.) of air containing the amounts of o-xylene (which is 97 percent by weight pure) given in the Table below, are passed per hour downward through the tube. The results summarized in the Table below are obtained (yield means phthalic anhydride obtained, in percent by weight based on 100% pure o-xylene or naphthalene):

| Concentration (g) of o-xylene/cubic meter (S.T.P.) of air | Salt bath temperature ° C | Yield, % by weight | Phthalide content in the crude phthalic anhydride % |
|---|---|---|---|
| 36.8 | 381 | 114.1 | traces |
| 50.1 | 374 | 113.8 | 0.001 |
| 60.3 | 362 | 114.0 | 0.003 |

COMPARATIVE EXPERIMENT

If only catalyst II is employed, as a layer 2.80 m high, and the oxidation is carried out at 375° C and at a concentration of 37.5 g of o-xylene per cubic meter (S.T.P.) of air, phthalic anhydride is obtained in a yield of 106 percent by weight and the product contains less than 0.001% of phthalide. In this case, o-xylene concentrations of more than 42 g lead to damage of the catalyst, because of the high peak temperatures reached.

If only the rubidium-containing catalyst I is used, the results shown in the Table below are obtained:

| Concentration (g) of o-xylene/cubic meter (S.T.P.) | Salt bath temperature ° C | Yield, % by weight | Phthalide content in the crude phthalic anhydride % |
|---|---|---|---|
| 37.1 | 402 | 114.5 | 0.06 |
| 58.5 | 378 | 114.1 | 0.12 |

EXAMPLE 2

The procedure described in Example 1 is followed, but instead of o-xylene, naphthalene is oxidized. The amount of air passed through the catalyst tube per hour is 4 cubic meters (S.T.P.) and the naphthalene content of the air is given in the Table below. The naphthalene employed is 99.1% pure and has a sulfur content of 0.4%. The results summarized in the Table which follows are obtained:

| Naphthalene concentration g of naphthalene/cubic meter (S.T.P.) of air | Salt bath temperature ° C | Yield, % by weight | Naphthoquinone in the crude phthalic anhydride % |
|---|---|---|---|
| 36.1 | 396 | 100 | 0.11 |
| 43.0 | 381 | 99.5 | 0.14 |
| 49.2 | 376 | 99.1 | 0.14 |

If only the rubidium-containing catalyst I is employed, as a layer 2.80 m high, phthalic anhydride is obtained in a yield of 102 percent by weight, but the product contains 2.3% of naphthoquinone.

If only the phosphorus-containing catalyst II is employed, phthalic anhydride is obtained in a yield of 90 percent by weight, and the product contains 0.04% of naphthoquinone.

We claim:

1. A process for the manufacture of phthalic anhydride by oxidizing o-xylene and/or naphthalene with oxygen over a supported catalyst coated with a catalytic composition containing vanadium pentoxide and titanium dioxide, at from 340° to 500° C, wherein the o-xylene and/or naphthalene is passed with an oxygen-containing carrier gas over the catalyst, and wherein the catalyst in the first 25–50 percent by volume of the total catalyst volume, in the direction of flow of the mixture of o-xylene and/or naphthalene and carrier gas, contains from 0.01 to 0.3 percent by weight, based on titanium dioxide, of rubidium, but no phosphorus, in the active composition, whilst the remainder of the catalyst contains from 0.02 to 0.8 percent by weight, based on titanium dioxide, of phosphorus, but no rubidium, in the active composition.

2. A process as claimed in claim 1, wherein the phosphorus-free catalyst accounts for the first 30–45 percent of the catalyst volume and the rubidium-free catalyst accounts for the remaining catalyst volume.

3. A process as claimed in claim 1, wherein the phosphorus-free catalyst contains in the active composition from 0.05 to 0.22 percent by weight, based on titanium dioxide, of rubidium, and the rubidium-free catalyst contains in the active composition from 0.05 to 0.6 percent by weight, based on titanium dioxide, of phosphorus.

4. A process as claimed in claim 1, wherein the mixture of carrier gas and o-xylene and/or naphthalene contains from 44 to 100 g of o-xyleen and/or naphthalene per cubic meter (S.T.P.).

5. A process as claimed in claim 1 wherein said catalyst in said first 25–50 percent by volume, excluding the support, consists essentially of 1 to 30 percent by weight of vanadium pentoxide, 70 to 99 percent by weight of titanium dioxide, and 0.01 to 0.3 percent by weight, based on the titanium dioxide, of rubidium and said remainder of said catalyst, excluding the support, consists essentially of 1 to 30 percent by weight of vanadium pentoxide, 70 to 99 percent by weight of titanium dioxide, and 0.02 to 0.8 percent by weight, based on the titanium dioxide, of phosphorus.

* * * * *

UNITED STATES PATENT AND TRADEMARK OFFICE
CERTIFICATE OF CORRECTION

PATENT NO. : 4,077,984

DATED : March 7, 1978

INVENTOR(S) : Kurt Blechschmitt et al.

It is certified that error appears in the above-identified patent and that said Letters Patent are hereby corrected as shown below:

IN THE TITLE: "o-XYLENE" should be -- O-XYLENE --;

Col. 6, line 12, "o-xyleen" should read -- -o-xylene --.

Signed and Sealed this

Nineteenth Day of December 1978

[SEAL]

Attest:

RUTH C. MASON
Attesting Officer

DONALD W. BANNER
Commissioner of Patents and Trademarks